United States Patent [19]

Bringhurst et al.

[11] Plant 4,490

[45] Nov. 27, 1979

[54] STRAWBERRY PLANT

[75] Inventors: Royce S. Bringhurst, Davis; Victor Voth, Santa Ana, both of Calif.

[73] Assignee: The Regents of the University of California, Berkeley, Calif.

[21] Appl. No.: 953,817

[22] Filed: Oct. 23, 1978

[51] Int. Cl.[2] ..... A01H 5/03

[52] U.S. Cl. ..... Plt./49

[58] Field of Search ..... Plt./49, 48

*Primary Examiner*—Robert E. Bagwill

*Attorney, Agent, or Firm*—Townsend and Townsend

[57] ABSTRACT

A new and distinct variety of strawberry plant of a short-day type characterized by its good yield throughout California but best performance in winter plantings in Coastal Southernn California where the variety produces a large crop of early high quality fruit of exceptionally fine appearance. Plants are vigorous and prolific runner makers and tend to generate more runners than Tufts in fruit plantings. Heavy flowering commences earlier than Tufts or Tioga in winter plantings in Coastal Southernn California. Fruit is long, conic and particularly smooth and glossy with some tending to be flat wedged. The flavor is equal to or better than the best California cultivars and berries are adequate for shipping when winter planted.

2 Drawing Figures

This invention relates to a new and distinctive short-day type strawberry cultivar designated as C38 which is the result of a cross between "Tufts" (U.S. Plant Pat. No. 3,561) and "Albritton" (not patented).

C38 first fruited at the University of California, South Coast Field Station, Santa Ana in 1973 where it was selected and designated originally as Cal 71.27-601.

C38 has since been tested with favorable results and asexually reproduced by runners at various University of California Field Stations and facilities and has also been favorably tested in a limited way in growers fields under strict control. Meristem originated virus negative stock for asexual reproduction is under development at the University of California.

FIG. 1 of the accompanying photographic color reproductions shows typical growth, flowering and fruiting characteristics of C38 in a winter planting in Southern California at mid-season.

Figure 1:
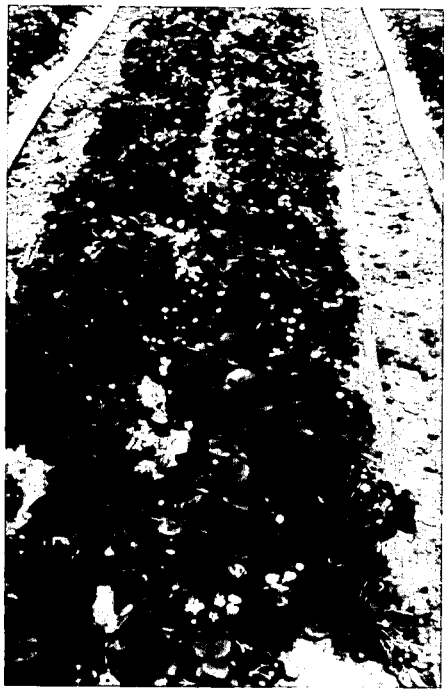
Figure 2:
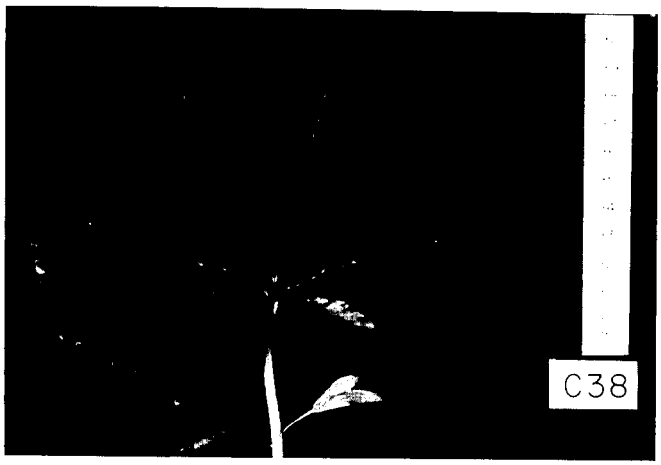
FIG. 2 shows a typical mid-summer mature leaf from a winter planted plant.
Figure 3:
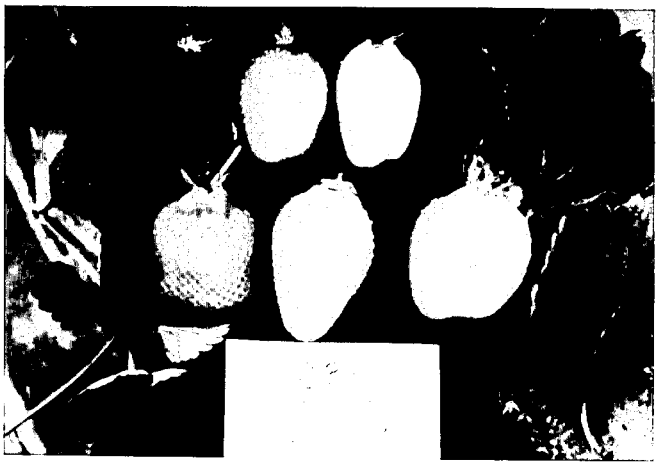
FIG. 3 shows typical mid-season fruit of C38 with a longitudinal section view.

C38 has yielded well throughout California but has performed best in winter plantings in coastal Southernn California where it has produced a large crop of early high quality fruit of exceptionally fine appearance. The plants tend to get too large for summer planting. Yield trials have demonstrated that it is likely to produce as much or more fruit in winter plantings in Southernn California during the most desirable part of the season than the heavy yielding California cultivars "Tioga" (not patented) and "Tufts".

The distinctive characteristics of this new strawberry cultivar described in detail below were observed upon its discovery and/or through the test period.

DESCRIPTION

Plants and foliage: C38 plants are semi erect in growth habit, somewhat similar to "Tufts" but ultimately larger in size than either "Tioga" or "Tufts". Bract leaves occur on almost all petioles of winter planted plants and about 60% of those of summer planted plants, about the same as "Tufts". Leaflets of C38 are about the same size as those of "Tioga" or "Tufts" and are lighter and slightly less yellow than those of "Tioga" but darker than those of "Tufts" about 5 GY 5/6 vs. 2.5 GY 4/3 and 7.5 GY 5/7, respectively (Munsell Color System — Nickerson Color Fan). The leaflets have almost as many serrations as those of "Tufts" (av of ± 11/half blade vs. ± 12 for "Tufts") more than those for "Tioga" or "Aiko" (av of ± 10/half blade) as averaged over the half blades of leaves on mid-season mature plants at Watsonville. The plants are very vigorous and C38 is a prolific runner maker in the nursery. C38 tends to generate more runners than "TuftS" in fruit plantings.

Isozymes in leaf extracts — Phosphoglucose isomerase (PGI): C38 gave a very slow 3 banded pattern, unique among all cultivars and selections tested; 25/35 35/35 35/35 35/35 mm, different than the single banded pattern of 'Tioga', the slow 3 banded pattern of 'Tufts' and the 5 banded pattern of "Aiko" (Scandalios. 1969. Biochem. Genet. 3:37-79).

Flowering and flowers: C38 is a standard short-day type that commences heavy flowering earlier than "Tufts" or "Tioga" in winter plantings in coastal Southernn California. Inflorescences are about as long as those of "Tufts", much longer than "Aiko" or "Tioga". The flowers are highly self fertile with ample pollen throughout the season.

Fruit and fruiting: C38 has long conic particularly smooth fruit, somewhat hollow centered with some of it tending to be flat wedged but not nearly as much so as "Tufts". Almost all fruit has a small neck. The skin color of C38 is almost the same as that of "Tioga" about 7.5 R 4.5/12 vs. 7.5 R 4.5/13 on "Tioga" (ibid). The finish is glossy and the flesh color is similar to that of the skin, except for a distinctly lighter area near the core. The calyx is particularly small and distinctly reflexed. The achenes are positioned about flush with the surface similar to "Tioga". The fruit is slightly less firm and less durable than that of "Aiko", "Tioga" or "Tufts" giving penetrometer readings of ± 6.3 vs. ± 6.7 for the three cultivars at Watsonville. The fruit has averaged about as large in size as that of "Tufts" in most tests, typically about 20 g/fr.

Fruit quality — Ascorbic acid: C38 averaged ± 53 mg/100 g of fresh fruit, greater than "Tioga" (± 40) or "Tufts" (± 45) and less than "Aiko" (± 60) as tested by the method of Loeffler and Ponting. 1942. J. Ind. and Engin. Chem. 14:846. Soluble solids: C38 averaged ± 8.8%, not significantly different from "Aiko", "Tioga" or "Tufts" according to our measurement on mid-summer Watsonville fruit. The flavor of C38 is equal to or better than that of the best important California cultivars in our opinion. Many have judged it exceptional. C38 is adequate as a shipping fruit from winter plantings and should be useful for processing.

We claim:

1. The new and distinct variety of strawberry plant herein described and illustrated, and identified by the characteristics enumerated above.

* * * * *